United States Patent [19]

Löwe et al.

[11] Patent Number: 5,766,576
[45] Date of Patent: Jun. 16, 1998

[54] OXIDATION HAIR DYE COMPOSITIONS CONTAINING 3,4,5-TRIAMINOPYRAZOLE DERIVATIVES AND 3,4,5-TRIAMINOPYRAZOLE DERIVATIVES

[75] Inventors: Isolde Löwe, Bensheim; Stefan Gerstung, Tann; Wolfgang R. Balzer, Alsbach, all of Germany

[73] Assignee: Wella Aktiengesellschaft, Darmstadt, Germany

[21] Appl. No.: 711,229

[22] Filed: Sep. 9, 1996

[30] Foreign Application Priority Data

Nov. 25, 1995 [DE] Germany .................. 195 43 988.0

[51] Int. Cl.⁶ .............. A61K 7/13; A61K 7/135; A01N 43/64
[52] U.S. Cl. .............. 424/62; 424/70.1; 424/70.6; 514/407; 548/371.4; 548/372.5
[58] Field of Search .............. 424/62, 70.6, 70.1; 514/407; 548/371.4, 372.5

[56] References Cited

U.S. PATENT DOCUMENTS

| 3,303,200 | 2/1967 | Wolf et al. ................ 548/372.5 |
| 5,380,340 | 1/1995 | Neunhoeffer et al. ........... 8/409 |
| 5,500,439 | 3/1996 | Ulrich et al. ................ 514/404 |

*Primary Examiner*—Michael P. Woodward
*Assistant Examiner*—Mary K. Zeman
*Attorney, Agent, or Firm*—Michael J. Striker

[57] ABSTRACT

The oxidation hair dye composition for oxidative dyeing of hair is based on a combination of developer substance and coupler substance and contains at least one 3,4,5-triaminopyrazole derivative compound selected from the group consisting of 1-methyl-3,4,5-triaminopyrazole, 3,5-diamino-1-methyl-4-methylaminopyrazole, 3,5-diamino-4-(2'-hydroxyethyl) amino-1-methylpyrazole and physiologically compatible, water-soluble salts of the foregoing pyrazole derivative compounds, as the developer substance. The invention also includes novel 3,4,5-triaminopyrazole derivative compounds.

5 Claims, No Drawings

OXIDATION HAIR DYE COMPOSITIONS CONTAINING 3,4,5-TRIAMINOPYRAZOLE DERIVATIVES AND 3,4,5-TRIAMINOPYRAZOLE DERIVATIVES

BACKGROUND OF THE INVENTION

The present invention relates to oxidation hair dye compositions based on 3,4,5-triaminopyrazole derivatives as developer substances and new 3,4,5-triaminopyrazole derivatives.

Oxidation hair dye compounds have acquired considerable importance in the field of hair dyeing. The color of the dyed hair arises because of a reaction of certain developer substances with certain coupler substances in the presence of an oxidizing agent.

Particularly 2,5-diaminotoluene, 2,5-diaminophenylethyl alcohol, p-aminophenol and 1,4-diaminobenzene are used as developer substances. Resorcinol, 4-chlororesorcinol, 1-naphthol, 3-aminophenol, 5-amino-2-methylphenol and derivatives of m-phenylenediamines are advantageously used as coupler substances.

There are numerous special requirements for oxidation hair dye compounds, which are used for dyeing human hair. They must be unobjectionable in regard to toxicological and dermatological considerations and must provide the desired dye color intensities. Satisfactory light-, permanent wave- and acid fastness is required for dyed hair colors as well as a fastness to friction or rubbing. The colors of the dyed hair must remain stable under action of light, friction and chemical agents for at least 4 to 6 weeks. Furthermore a broad palette of different color shades and tones must be provided by various combinations of suitable developer and coupler substances. Above all 4-aminophenol, alone or in mixture with different developer substances, is used in combination with suitable coupler substances to obtain natural and particularly fashionable shades in the red range.

Reasons regarding physiological compatibility have developed which suggest avoiding use of the 4-aminophenol developer compound recently primarily used for the red range of the color spectrum, while the more recently currently recommended developer substances, such as pyrimidine derivatives, are not completely satisfactory.

The pyrazole derivatives described in German Published Patent Application DE-OS 21 60 317, such as 3-amino-1-phenyl-2-pyrazolon-5, dye hair only in greatly reduced color depth or intensity, unusable in practical hair dyeing methods.

SUMMARY OF THE INVENTION

It is an object of the present invention to provide an oxidation hair dye composition which contains a developer substance for the red range, which has very good physiological compatibility and when used together with conventional coupler substances dyes the hair in brilliant red shades having a high color intensity.

According to the invention, the oxidation hair dye composition is based on a developer-coupler substance combination in which a 3,4,5-triaminopyrazole derivative of formula (I)

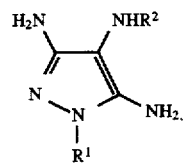

acts a developer substance, wherein $R^1$ and $R^2$ each independently represent hydrogen, an alkyl group with 1 to 4 carbon atoms or a hydroxyalkyl group with 2 to 4 carbon atoms, or its physiologically compatible, water-soluble salt.

The oxidation hair dye composition according to the invention attains the objects of the invention in an outstanding manner.

The developer substances of formula (I), of which 1-methyl-3,4,5-triaminopyrazole, 3,5-diamino-1-methyl-4-methylaminopyrazole and 3,5-diamino-4-(2'-hydroxyethyl)-amino-1-methyl-pyrazole are preferred, should be contained in the hair dye composition according to the invention in an amount of 0.01 to 3.0 percent by weight, advantageously in an amount of from 0.1 to 2.5 percent by weight.

Although these new developer substances of the formula (I) having the advantageous properties may be used alone, they may also be used together with known developer substances, such as 1,4-diaminobenzene, 2,5-diaminotoluene or 2,5-diaminophenylethyl alcohol.

The following compounds can be used as coupler substances: α-naphthol, resorcinol, 4-chlororesorcinol, 2-methylresorcinol, 2-amino-4-(2'-hydroxyethyl) aminoanisole, 2,4-diaminophenyl alcohol, m-phenylenediamine, 5-amino-2-methylphenol, 2,4-diaminophenoxyethanol, 4-amino-2-hydroxyphenoxyethanol, 3-aminophenol, 3-amino-2-methylphenol, 4-hydroxy-1,2-methylenedioxybenzene, 4-amino-1,2-methylene-dioxybenzene, 4-(2'-hydroxyethyl) amino-1,2-methylene-dioxybenzene, 2,4-diamino-5-fluorotoluene, 4-amino-5-fluoro-2-hydroxytoluene, 2,4-diaminobenzyl alcohol, 2,4-diamino-phentole, 2,4-diamino-5-methylphenetole, 4-hydroxyindole, 3-amino-5-hydroxy-2,6-dimethoxypyridine and 3,5-diamino-2,6-dimethoxypyridine.

The coupler and developer substances can be contained individually in the oxidation hair dye composition according to the invention or in a mixture with each other.

The total amount of the developer-coupler combination in the hair dye composition described here amounts to from 0.1 to 5.0 percent by weight, but an amount of from 0.5 to 4.0 percent by weight is particularly preferred. The developer components are advantageously present in approximately equimolar amounts in relation to the coupler components. It is however not disadvantageous if the developer components are present in a certain excess relative to the coupler components, and vice versa.

The hair dye composition according to the invention may also contain auxiliary dye compounds, such as 6-amino-2-methylphenol and 2-amino-5-methylphenol, and conventional direct dye compounds, such as triphenylmethane dye compounds, for example 4-[(4'-aminophenyl)-(4'-imino-2", 5"-cyclohexadien-1"-yliden)methyl]-2-methylaminobenzene monohydrochloride (C.I. 42 510) and 4-[(4'-amino-3'-methylphenyl)-(4"-imino-3"-methyl-2",5"-cyclohexadien-1"-yliden)methyl]-2-methylaminobenzene monohydrochloride (C.I.42 520); aromatic nitrodye compounds, such as 2-nitro-1,4-diaminobenzene, 2-amino-4-nitrophenol, 2-amino-5-nitrophenol, 2-amino-4,6-dinitrophenol, 2-amino-5-(2'-hydroxyethyl) aminonitrobenzene and 2-methylamino-5-bis-(2'- hydroxyethyl)aminonitrobenzene; azo dye compounds, for example, such as 6-[(4'-aminophenyl)azo]-5-hydroxynaphthalen-1-sulfonic acid sodium salt (C.I. 14 805) and disperse dye compounds, for example, 1,4-diaminoanthraquinone and 1,4,5,8-tetraaminoanthraquinone. The oxidation hair dye composition according to the invention can contain these dye components in amounts of about 0.1 to 4.0 per cent by weight.

Understandably the coupler and developer substances and the other dye components, in so far as they are bases, can also be used in the form of their physiologically compatible salts with organic or inorganic acids, such as hydrochloric or sulfuric acid, and/or—in so far as they contain aromatic OH groups—in the form of salts with bases, for example alkali phenolates.

Moreover additional conventional additives, for example antioxidants, such as ascorbic acid, thioglycolic acid or sodium sulfite, and perfume oils, complex formers, wetting agents, emulsifiers, thickeners and care substances, may be contained in the composition according to the invention.

The oxidation hair dye composition according to the invention may be in the form of a solution, especially an aqueous or aqueous-alcoholic solution. However preparations in the form of a cream, a gel or an emulsion are particularly preferred. Their composition may be a mixture of dye components with the conventional cosmetic ingredients used in this type of composition.

The conventional cosmetic ingredients used in solutions, creams, emulsions or gels are, for example, solvents, such as water, lower aliphatic alcohols, e.g., ethanol, propanol or isopropanol, glycerol or glycols, such as 1,2-propyleneglycol; wetting agents or emulsifiers from the classes of anionic, cationic, amphoteric or nonionic surface active substances, such as fatty alcohol sulfates, ethoxylated fatty alcohol sulfates, alkylsulfonates, alkylbenzenesulfonates, alkyltrimethyl-ammonium salts, alkyl betaines, ethoxylated fatty alcohols, ethoxylated nonylphenols, fatty acid alkanolamides, ethoxylated fatty acid esters; thickeners, such as higher fatty alcohols, starches, cellulose derivatives, petrolatum, paraffin oil and fatty acids, and care substances, such as cationic resins, lanolin derivatives, cholesterol, pantothenic acid and betaine. The above-mentioned ingredients are used in amounts appropriate for their purpose, for example the wetting agents and emulsifiers in concentrations of about 0.5 to 30 percent by weight, the thickeners in amounts of about 0.1 to 25 percent by weight and the care substances in a concentration of about 0.1 to 5.0 percent by weight.

The oxidation hair dye composition according to the invention may react weakly acidic, neutral or basic according to its composition. Particularly in preferred embodiments it has a pH of from 6.0 to 11.5, the basic values being adjusted with ammonia. Also organic amines, e.g. monoethanolamine and triethanolamine, also inorganic bases such as sodium hydroxide and potassium hydroxide, can be used to adjust the pH. Phosphoric acid, acetic acid or other organic acids such as citric acid or tartaric acid may be used to adjust the pH in the acid range.

To oxidatively dye hair the above-described hair dye compounds are mixed immediately prior to use with an oxidizing agent and a sufficient amount of the hair dyeing mixture is applied to the hair, according to the amount of the hair, usually about 60 to 200 g, for the hair dye treatment.

As oxidizing agent for the development of the hair dyes hydrogen peroxide or its addition compounds with urea, melamine or sodium borate in the form of a 3 to 12 percent by weight, advantageously 6 percent by weight, aqueous solution may be used. When a 6 percent by weight hydrogen peroxide solution is used as oxidizing agent, the weight ratio of hair dye compounds to oxidizing agent amounts to from 5:1 to 1:2, advantageously however 1:1. Larger amounts of oxidizing agents are used, above all, with higher dye concentration in the oxidative hair dye composition or when a comparatively strong bleaching of the hair is intended at the same time. The hair dyeing mixture is allowed to act on the hair at 15° to 50° C. for about 10 to 45 minutes, advantageously for 30 minutes, then rinsed from the hair with water and dried. If necessary in connection with this rinsing the hair is washed with a shampoo and eventually after-rinsed with a weak organic acid, such as citric acid or tartaric acid. Subsequently the hair is dried.

The 3,4,5-triaminopyrazole of formula (I) contained in the hair dye composition according to the invention may be made by the following reaction scheme:

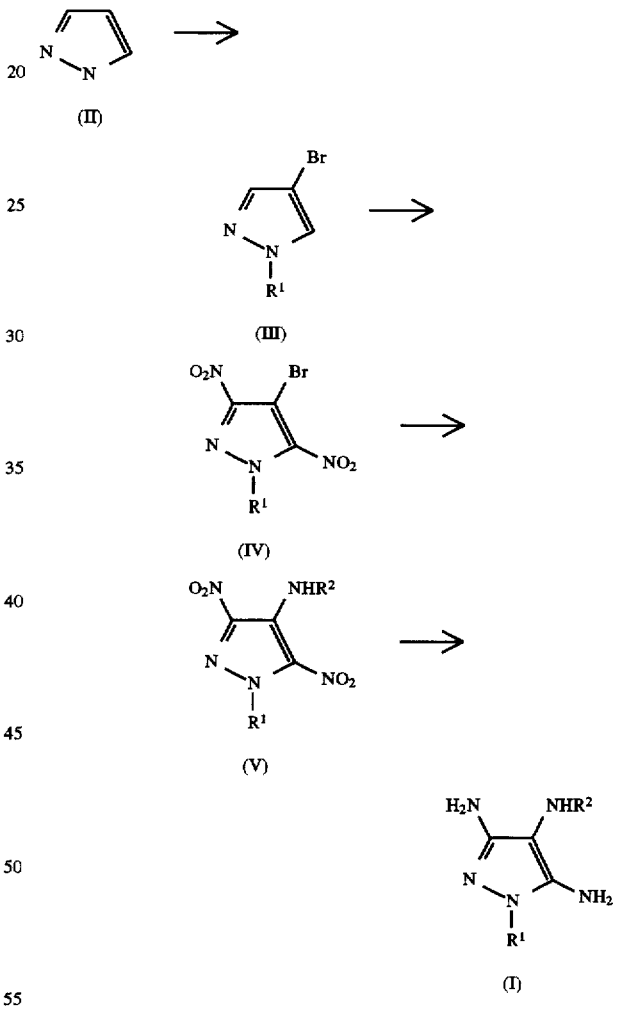

The salts of the compound of formula (I) should be used in the oxidative hair dye composition either as free bases or in the form of their physiologically compatible salts with inorganic or organic acids, for example hydrochloric acid, lactic acid or citric acid. The compounds of formula (I) are sufficiently soluble in water and they have outstanding storage stability, especially as ingredients of the hair dye composition described here.

The hair dye composition according to the invention with a content of 3,4,5-triaminopyrazole derivatives as developer substance provides outstanding color fastness, particularly light-, wash- and friction-fastness.

In regard to its color characteristics the hair dye composition according to the invention provides possibilities, which largely go beyond the prior art by a replacement of the conventionally used 4-aminophenol. Brilliant red shades may be produced with extraordinary color intensities, which has not been possible with prior art dye ingredients. Besides natural color shades can be produced in the highly fashionable range also by using a combination of the hair dyeing agents of the invention with suitable coupler components. If it were not for that, additional developer components would be required of the p-phenylenediamine type.

The very good hair dyeing properties of the hair dye composition according to the present invention also allow this composition to dye gray chemically undamaged hair with satisfactory color coverage without problems.

The present invention also includes novel 3,4,5-triaminopyrazole derivatives of the general formula (I), particularly 1-methyl-3,4,5-triaminopyrazole, 3,5-diamino-1-methyl-4-methylaminopyrazole and 3,5-diamino-4-(2'-hydroxyethyl)amino-1-methylpyrazole.

The disclosure in German Patent Application 195 43 988.0, which also discloses the instant invention and forms the basis for a claim of priority for it under 35 U.S.C. 119, is incorporated here by reference.

The subject matter of the invention is now illustrated in greater detail by the following examples, which should not be considered as limiting the concept of the invention expressed in the appended claims.

EXAMPLES

Example 1: Synthesis of 4-amino-3,5-dinitro-1-methylpyrazole of the formula (V)
General Procedure 5 g (20 mmol) 4-bromo-3,5-dinitro-1-methylpyrazole are mixed in 20 ml dimethylsulfoxide (DMSO) with a three-fold molar excess of alkylamine and heated for 2 hours in a water bath. Subsequently the reaction product is poured into ice, the precipitate filtered and recrystallized from ethanol.

Particular Examples 1a) to 1c)

1a) 4-benzylamino-3,5-dinitro-1-methylpyrazole
  amine used: benzylamine
  3.46 g (63% of the theoretical yield) of 4-benzylamino-3,5-dinitro-1-methylpyrazole were obtained in the form of yellow crystals.
  Melting point: 92° C.

1b) 4-methylamino-3,5-dinitro-1-methylpyrazole
  amine used: methylamine
  2.71 g(67% of the theoretical yield) of 4-methylamino-3,5-dinitro-1-methylpyrazole in the form of yellow crystals were obtained.
  Melting point: 128° C.

1c) 4-(2'-hydroxyethyl)amino-3,5-dinitro-1-methylpyrazole
  amine used: ethanolamine
  2.22 g(50% of the theoretical yield) of 4-(2'-hydroxyethyl)amino-3,5-dinitro-1-methylpyrazole in the form of yellow crystals were obtained.
  Melting point: 101 to 103° C.

Example 2: Synthesis of 1-methyl-3,4,5-triaminopyrazole of formula (I)
General Procedure 10 mmol of the corresponding nitro compound 1a, 1b, or 1c are hydrogenated in methanol using a Palladium-activated carbon catalyst (10%) at room temperature (20° to 30° C.). After ending the reaction the product is filtered off from the catalyst in a mixture of sulfuric acid and water. After addition of methanol the corresponding sulfate is precipitated as a crystalline product.

Particular Examples 2a) to 2c)

2a) 1-methyl-3,4,5-triaminopyrazole sulfate
  Nitrocompound 1a was used.
  2 g (89% of the theoretical yield) of 1-methyl-3,4,5-triaminopyrazole sulfate was obtained in the form of colorless crystals, which melted with decomposition at 205° C.

2b) 3,5-diamino-1-methyl-4-methylaminopyrazole sulfate
  2 g (84% of the theoretical yield) of 3,5-diamino-1-methyl-4-methylaminopyrazole sulfate was obtained in the form of colorless crystals, which melted with decomposition at 214° C.

2c) 3,5-diamino-1-methyl-4-(2'-hydroxyethyl)amino-1-methylpyrazole sulfate
  1.6 g (59% of the theoretical yield) of 3,5-diamino-1-methyl-4-(2'-hydroxyethyl)amino-1-methylaminopyrazole sulfate was obtained in the form of colorless crystals, which melted with decomposition at 198° C.

Exemplary Hair Dye Compositions

Example 3: Hair Dye Composition in the form of a Cream

| | |
|---|---|
| 1.40 g | 1-methyl-3,4,5-triaminopyrazole sulfate |
| 0.67 g | α-naphthol |
| 0.28 g | 2-amino-4-(2'-hydroxyethyl)aminoanisole sulfate |
| 15.00 g | cetyl alcohol |
| 3.50 g | sodium lauryl alcohol diglycol ether sulfate (28% aqueous solution) |
| 0.30 g | sodium sulfite, water-free |
| 0.19 g | sodium hydroxide(10 percent aqueous solution) |
| 1.77 g | ammonia (25 percent aqueous solution) |
| 76.89 g | water |
| 100.0 g | |

50 g of the above-described hair dye composition are mixed immediately prior to use with 50 g of hydrogen peroxide solution (6%) and the mixture is subsequently applied to blond natural hair. After an acting time of 30 minutes at 40° C. the hair is rinsed with water and dried. The dyed hair had an intense auburn color shade.

Example 4: Hair Dye Composition in the form of a Cream

| | |
|---|---|
| 1.44 g | 3,5-diamino-1-methyl-4-methylaminopyrazole sulfate |
| 0.31 g | 5-amino-2-methylphenol |
| 0.36 g | α-naphthol |
| 15.00 g | cetyl alcohol |
| 3.50 g | sodium lauryl alcohol diglycol ether sulfate (28% aqueous solution) |
| 0.30 g | sodium sulfite, water-free |
| 0.19 g | sodium hydroxide(10 percent aqueous solution) |
| 1.00 g | ammonia (25 percent aqueous solution) |
| 77.90 g | water |
| 100.0 g | |

Immediately prior to use 50 g of the previously described hair dye composition was mixed with 50 g of hydrogen peroxide solution and the mixture was allowed to act on natural blond hair for 30 minutes at 40° C. The hair was rinsed with water and dried. The hair was dyed an intense purple color.

Examples 5 to 17: Hair Dye Compositions
Hair dye solutions of the following composition were prepared:

| | |
|---|---|
| 0.025 mol | developer according to table I |
| 0.025 mol | coupler according to table I |
| 10.00 g | lauryl alcohol diglycol ether sulfate sodium salt (28% by weight aqueous solution) |
| 10.00 g | ammonia (22 percent aqueous solution) |
| ad 100.00 g | water |
| 100.00 | |

The hair dye solutions were prepared according to example 3 and applied to 90% gray, human hair. The resulting colors are tabulated in the following Table I.

TABLE I. HAIR COLORS PRODUCED BY THE HAIR DYE COMPOSITIONS EXAMPLES 5 to 7

| Expl. | Developer of formula I | Coupler | Color |
|---|---|---|---|
| 5 | 2a) | 5-amino-2-methylphenol | bright red |
| 6 | 2b) | 5-amino-2-methylphenol | red |
| 7 | 2c) | 5-amino-2-methylphenol | red |
| 8 | 2a) | 3-aminophenol | orange |
| 9 | 2b) | 3-aminophenol | orange |
| 10 | 2c) | 3-aminophenol | orange-red |
| 11 | 2a) | 2-amino-4-(2'-hydroxyethyl)aminoanisole sulfate | dark blue-gray |
| 12 | 2b) | 2-amino-4-(2'-hydroxyethyl)aminoanisole sulfate | blue-gray |
| 13 | 2c) | 2-amino-4-(2'-hydroxyethyl)aminoanisole sulfate | gray-violet |
| 14 | 2a) | α-naphthol | golden-yellow |
| 15 | 2b) | α-naphthol | golden-orange |
| 16 | 2a) | 2,4-diamino-5-fluorotoluene | dark violet |
| 17 | 2b) | 2,4-diamino-5-fluorotoluene | violet |

All percentages, unless otherwise indicated, are percentages by weight.

What is claimed is:

1. An oxidation hair dye composition for oxidative dyeing of hair comprising a combination of developer substance and coupler substance, said oxidation hair dye composition containing at least one developer compound selected from the group consisting of 1-methyl-3,4,5-triaminopyrazole, 3,5-diamino-1-methyl-4-methylaminopyrazole, 3,5-diamino-4-(2'-hydroxyethyl)amino-1-methylpyrazole and physiologically compatible, water-soluble salts thereof, as the developer substance.

2. The oxidation hair dye composition as defined in claim 1, wherein the at least one developer compound is present in an amount of from 0.01 to 3.0 percent by weight.

3. The oxidation hair dye composition as defined in claim 1, further comprising at least one coupler compound selected from the group consisting of α-naphthol, resorcinol, 4-chlororesorcinol, 2-methylresorcinol, 2-amino-4-(2'-hydroxyethyl)aminoanisole, 5-amino-2-methylphenol, 3-amino-2-methylphenol, 4-hydroxy-1,2-methylenedioxybenzene, 4-amino-1,2-methylenedioxybenzene, 4-(2'-hydroxyethyl)amino-1,2-methylenedioxybenzene, 2,4-diamino-phentole, 2,4-diamino-5-methylphenetole, 2,4-diamino-5-fluorotoluene, 4-amino-5-fluoro-2-hydroxytoluene, 2,4-diaminobenzyl alcohol, m-phenylenediamine, 2,4-diaminophenoxyethanol, 4-hydroxy-indole, 3-amino-5-hydroxy-2,6-dimethoxypyridine and 3,5-diamino-2,6-dimethoxypyridine, as the coupler substance.

4. The oxidation hair dye composition as defined in claim 1, wherein a total amount of the combination of the developer substance and the coupler substance present amounts to from 0.1 to 5.0 percent by weight.

5. The oxidation hair dye composition as defined in claim 1, further comprising at least one auxiliary hair dye compound selected from the group consisting of 6-amino-2-methylphenol, 2-amino-5-methylphenol, 2-amino-4-[(4'-aminophenyl)-(4'-imino-2",5"-cyclohexadien-1"-yliden)methyl]-2-methylaminobenzene monohydrochloride (C.I. 42 510), 4-[(4'-amino-3'-methylphenyl)-(4"-imino-3"-methyl-2",5"-cyclohexadien-1"-yliden)methyl]-2-methylaminobenzene monohydrochloride (C.I.42 520), 2-nitro-1,4-diaminobenzene, 2-amino-4-nitrophenol, 2-amino-5-nitrophenol, 2-amino-4,6-dinitrophenol, 2-amino-5-(2'-hydroxyethyl)aminonitrobenzene, 2-methylamino-5-bis-(2'-hydroxyethyl)aminonitrobenzene, 6-[(4'-aminophenyl)azo]-5-hydroxynaphthalen-1-sulfonic acid sodium salt (C.I. 14 805), 1,4-diaminoanthraquinone and 1,4,5,8-tetraaminoanthraquinone.

* * * * *